United States Patent
Hearn et al.

(10) Patent No.: US 10,542,778 B2
(45) Date of Patent: Jan. 28, 2020

(54) INHALER

(71) Applicant: Kind Consumer Limited, London (GB)

(72) Inventors: Alex Hearn, London (GB); Iain McDerment, Hertfordshire (GB); Khine Zaw Nyein, Middlesex (GB); David John Cottenden, Hertfordshire (GB)

(73) Assignee: KIND CONSUMER LIMITED, London (GB)

( * ) Notice: Subject to any disclaimer, the term of this patent is extended or adjusted under 35 U.S.C. 154(b) by 0 days.

(21) Appl. No.: 15/126,980

(22) PCT Filed: Mar. 19, 2015

(86) PCT No.: PCT/GB2015/050801
§ 371 (c)(1),
(2) Date: Sep. 16, 2016

(87) PCT Pub. No.: WO2015/140555
PCT Pub. Date: Sep. 24, 2015

(65) Prior Publication Data
US 2017/0086502 A1    Mar. 30, 2017

(30) Foreign Application Priority Data
Mar. 19, 2014    (GB) .................................. 1404942.3

(51) Int. Cl.
*A24F 47/00*    (2006.01)
*H02J 7/00*     (2006.01)
(Continued)

(52) U.S. Cl.
CPC .......... *A24F 47/008* (2013.01); *H02J 7/0054* (2013.01); *H02J 7/0063* (2013.01);
(Continued)

(58) Field of Classification Search
CPC ..... A24F 47/008; H02J 7/0054; H02J 7/0063; H02J 7/435
(Continued)

(56) References Cited

U.S. PATENT DOCUMENTS 4,393,884 A * 7/1983 Jacobs .................. A24F 47/002
                                                    128/200.23
4,527,572 A * 7/1985 Luke ..................... A24D 3/043
                                                    131/336
(Continued)

FOREIGN PATENT DOCUMENTS

CN    202774134 U    3/2013
CN    203302350 U    11/2013
(Continued)

OTHER PUBLICATIONS

International Search Report and Written Opinion dated Jun. 3, 2015 for Application No. PCT/GB2015/050801.
(Continued)

*Primary Examiner* — Alexander Gilman
(74) *Attorney, Agent, or Firm* — Patterson + Sheridan, LLP

(57)    ABSTRACT

A combination of an inhaler and a refill pack. The inhaler comprises a reservoir for an inhalable composition, a heating element and/or vibrating transducer to selectively volatilise at least some components of the composition and at least one inhaler capacitor arranged to supply electrical power to the heater and/or vibrating transducer when a user inhales from the inhaler. The refill pack comprises a refill reservoir of inhalable composition and a battery coupled to a refill capacitor, and is arranged to engage with the inhaler and to simultaneously refill the reservoir and recharge the inhaler capacitor from the refill capacitor. The invention also
(Continued)

extends to the inhaler and refill pack separately and to a method of refilling and recharging the inhaler.

20 Claims, 3 Drawing Sheets

(51) Int. Cl.
*H05B 1/02* (2006.01)
*H02J 7/34* (2006.01)
(52) U.S. Cl.
CPC ............ *H05B 1/0244* (2013.01); *H02J 7/345* (2013.01); *H05B 2203/021* (2013.01)
(58) Field of Classification Search
USPC ........................................................ 131/329
See application file for complete search history.

(56) References Cited

U.S. PATENT DOCUMENTS

| | | | | |
|---|---|---|---|---|
| 4,907,606 | A * | 3/1990 | Lilja | A24B 15/18 131/194 |
| 5,101,838 | A * | 4/1992 | Schwartz | A24F 47/002 131/273 |
| 6,637,430 | B1 * | 10/2003 | Voges | A61M 15/0065 128/200.14 |
| 9,668,522 | B2 * | 6/2017 | Memari | B65B 3/04 |
| 2010/0126517 | A1 * | 5/2010 | Groff | A24F 1/30 131/173 |
| 2010/0242975 | A1 * | 9/2010 | Hearn | A24F 47/002 131/273 |
| 2011/0094523 | A1 * | 4/2011 | Thorens | A24F 47/008 131/194 |
| 2011/0192408 | A1 * | 8/2011 | Inagaki | A24F 47/008 131/194 |
| 2011/0315152 | A1 * | 12/2011 | Hearn | A24F 47/002 131/273 |
| 2012/0048266 | A1 * | 3/2012 | Alelov | A61M 11/005 128/202.21 |
| 2012/0167906 | A1 * | 7/2012 | Gysland | A24F 47/008 131/328 |
| 2012/0227753 | A1 * | 9/2012 | Newton | A24F 47/008 131/347 |
| 2013/0037042 | A1 * | 2/2013 | Hearn | A24F 47/002 131/329 |
| 2013/0199550 | A1 * | 8/2013 | Ono | A24C 5/472 131/280 |
| 2013/0255702 | A1 * | 10/2013 | Griffith, Jr. | A24F 47/008 131/328 |
| 2013/0312739 | A1 * | 11/2013 | Rome | A24F 47/002 128/200.22 |
| 2014/0000638 | A1 | 1/2014 | Sebastian et al. | |
| 2014/0020697 | A1 * | 1/2014 | Liu | A24F 15/00 131/329 |
| 2014/0034070 | A1 | 2/2014 | Schennum | |
| 2014/0060554 | A1 * | 3/2014 | Collett | H05B 3/265 131/328 |
| 2014/0202472 | A1 * | 7/2014 | Levitz | A24F 13/22 131/187 |
| 2015/0040925 | A1 * | 2/2015 | Saleem | A24F 47/008 131/328 |
| 2015/0122276 | A1 * | 5/2015 | Johnson | A24D 3/04 131/329 |
| 2015/0128966 | A1 * | 5/2015 | Lord | A24F 47/002 131/328 |
| 2016/0128966 | A1 * | 5/2016 | Han | A61K 31/23 424/85.1 |
| 2016/0192713 | A1 * | 7/2016 | Memari | A24F 15/12 141/2 |
| 2016/0280450 | A1 * | 9/2016 | Hearn | A61M 15/0091 |
| 2017/0105449 | A1 * | 4/2017 | Hearn | B67D 7/0294 |

FOREIGN PATENT DOCUMENTS

| | | |
|---|---|---|
| CN | 203341005 U | 12/2013 |
| EP | 2454956 A1 | 5/2012 |
| GB | 2502053 A | 11/2013 |
| WO | 9409842 A1 | 5/1994 |
| WO | 2011095781 A1 | 8/2011 |
| WO | 2013040275 A1 | 3/2013 |

OTHER PUBLICATIONS

United Kingdom Search Report for Application No. GB1404942.3 dated Sep. 22, 2014.

* cited by examiner

INHALER

The present invention relates to an inhaler.

Conventional E-cigarettes have a volume of inhalable composition, a battery and a heating element to vaporise some of the composition as a user sucks on the end of the cigarette, the vaporised composition then being inhaled.

E-cigarettes are gaining increasing popularity as they provide an alternative to conventional smoking which eliminates the many carcinogens and toxic substances found in tobacco products.

E-cigarettes conventionally use an inhalable composition consisting of a high level of propylene glycol, glycerol, glycerin or glycol in which the nicotine (or alternative such as a flavouring) is solubilised. The high level of propylene glycol causes the composition to be viscous. This is beneficial as it can prevent unwanted evaporation of the composition out of the device and is usually contained in a cotton wadding, pad or other absorbent material. E-cigarettes generally comprise a heater or an ultrasonic atomiser which is in the vicinity of a small amount of the composition volume. Suction on the inlet end causes operation of the heater, and the substance in the vicinity of the heater is evaporated and inhaled. The relatively high viscosity of the composition ensures that the composition available to the heater is gradually replenished but generally prevents it from leaking from the absorbent material in the absence of heat.

While this is reasonably successful, there are two main drawbacks associated with electronic cigarettes. Firstly, the propylene glycol vaporises at a relatively high temperature such that this causes degradation of the composition generally used in E-cigarettes. This can lead to problems with dosage consistency and the presence of contaminants in the inhaled composition including the production of by-products such as formaldehyde, toluene and acrolein.

Secondly, the E-cigarettes require relatively high power to generate the high temperature. Moreover they normally require large batteries to deliver a total dose of vaporised composition to last the user the equivalent of between 20 to 40 cigarettes worth of inhalable composition. The cigarettes have the power to dispense at least one reservoir full of composition. As this large volume is dispensed at a high temperature, a large battery is required. Additionally since larger reservoirs and batteries are used, the nicotine dosage contained in E-cigarettes is high and potentially poses safety concerns when packaged in this format.

Broadly, such E-cigarettes can be divided into three categories, namely rechargeable, refillable and disposable. Those which are rechargeable come with a mains power adaptor. This is cumbersome for a user to carry around as it cannot readily fit into a pocket which is inconvenient. The relatively long recharge time is also inconvenient if a user only remembers that the charge has run down just before they go out.

There are also refillable E-cigarettes which require disassembly of the device and the replacement of the reservoir via a cartridge, liquid or absorbent material. However these are the subject of legal restrictions in many countries due to the availability of drug composition in unsealed containers. Moreover extra care is required in the process of replacing cartridges or material within the device, and extra effort is required by the user to refill which can be cumbersome and messy, especially if composition comes in contact with the skin.

A more recent development is a disposable cigarette. This is designed to last for a time equivalent to approximately 10-20 cigarettes, whereupon the cigarette and its container are thrown away. This is not environmentally friendly, particularly when the cigarette contains a relatively large battery and could be reused or recycled.

The present invention addresses some of the above problems.

EP 2454956 and WO 2013/040275 disclose E-cigarettes having batteries. These cigarettes are also provided with one or more capacitors which cooperate with the battery in order to quickly deliver a high power to the heater in order to vaporise the liquid.

US 2012/0227753 discloses a charger pack for an E-cigarette. This contains a relatively large battery which is able to recharge a battery or a capacitor in the cigarette. The cigarette is of a type which is disassembled into a number of components, all of which can be stored separately within the pack. The pack has the ability to recharge more than one cigarette at a time which suggests that the intention is for a relatively slow recharge which can be carried out while a previously charged body is used. The application contains no reference to the inhalable liquid. It is presumed that this is supplied as an E-liquid and that the cigarette is unscrewed to allow a reservoir within the E-cigarette to be filled up or for a replacement cartridge to be fitted.

According to a first aspect of the present invention, there is provided a combination of an inhaler and a refill pack, the inhaler comprising a reservoir for an inhalable composition, a heating element and/or vibrating transducer to selectively volatilise at least some components of the composition and at least one inhaler capacitor arranged to selectively supply electrical power to the heater and/or vibrating transducer when a user inhales from the inhaler; the refill pack comprising a refill reservoir of inhalable composition and a battery coupled to a refill capacitor, and being arranged to engage with the inhaler and to simultaneously refill the reservoir and recharge the inhaler capacitor from the refill capacitor.

By providing a refill pack which can simultaneously recharge the inhaler and refill the reservoir by engagement between the inhaler and the refill pack, the present invention provides a convenient way of replenishing not only the charge in the inhaler but also the composition.

This lends itself to an inhaler which can have a relatively small reservoir capacity which can be regularly refilled. The fact that the user has to return to the pack relatively frequently is beneficial for a number of reasons. With many conventional E-cigarettes, the user can simply go on inhaling from the cigarette without having to take any further action. As a consequence of this, they can smoke the equivalent of several cigarettes without being aware of it. Because it is convenient to refill and recharge, the present invention can be arranged to be replenished much more frequently, ideally after approximately the same number of puffs as are typically taken on a conventional cigarette, therefore limiting the intake and giving a cue to the user that they have reached the intended dose or equivalent dose of a conventional cigarette.

Further, because conventional E-cigarettes have a relatively high volume of reservoir, the control of dosage uniformity becomes difficult. In the early stages of use when the reservoir is relatively full, the E-cigarette can dispense several times the dosage that it does towards the end when the reservoir is depleted since active nicotine is commonly more volatile than the glycol excipient. Therefore over the course of the equivalent of 20-40 cigarettes, a user will experience fluctuations in dose, thereby delivering substantially over or under the therapeutic level to satisfy craving. Providing a pack with which the user must engage the inhaler to refill the reservoir and recharge the capacitor is a convenient way of regularly refilling the cigarette and allows a relatively small reservoir volume. The total amount of power required to volatilise and dispense the contents of the reservoir is much smaller. As a result of this, a capacitor, which tends to have a smaller power density than the battery of equivalent size can be used.

Because of the low power requirement of the inhaler as mentioned above, the capacitor can be recharged relatively quickly. Preferably the pack is arranged to fully recharge and refill the capacitor from empty in less than 30 seconds and preferably less than 10 seconds. Thus, rather than needing to wait for some time as in US 2012/0227753, the user can simply hold the cigarette in engagement with the refill pack for a matter of seconds while the cigarette is also refilled.

If a relatively large amount of power is required for the E-cigarette, it is possible that a battery could be provided in the E-cigarette in combination with the capacitor. However, our intention is that the total power requirement is small enough that the capacitor is the sole electrical power source on the E-cigarette.

Preferably, the total capacitance of the E-cigarette is 1 F to 350 F, preferably 1 to 50 F and most preferably 3 F to 7 F. At present, capacitors at these higher ratings are too large to fit in an inhaler the size of a cigarette, such that to accommodate these, a larger inhaler would be necessary. However, capacitor technology is developing rapidly, and it may soon be possible to achieve such a capacitor in a cigarette sized inhaler. The capacitor is preferably a super capacitor as this provides the highest energy density. There may be more than one capacitor in each E-cigarette.

The battery in the refill may be rechargeable. Due to the nature of the device and composition, the refill can charge the device a number of times, preferably more than 20 times. Additionally the inhaler can operate at a low enough power that enough energy can be transferred from a battery, yet it can still be small enough to be accommodated in a refill pack together with a refill reservoir and means for storing the inhaler whilst still maintaining the pack at a size comparable to that of a cigarette pack.

The refill reservoir may be pressurised, for example using a spring-loaded plunger which is released upon engagement of the inhaler with the pack in order to force the inhalable composition into the cigarette reservoir. Alternatively, the engagement of the inhaler with the refill pack is arranged to push against the reservoir thereby dispensing the composition into the inhaler reservoir.

As a further alternative, the refill reservoir may be pressurised with a propellant or a compressed gas, the inhaler reservoir having a closable refill valve and the refill pack having a complementary refill valve such that engagement of the inhaler with the pack will cause the two refill valves to open thereby allowing the pressurised composition to flow into the inhaler reservoir.

The refill pack is preferably configured such that it will automatically terminate the refill and recharge operations. This may be done by sensing some parameter associated with either (such as the duration or total flow rate for the refill, the duration, pressure transfill, transferred charge, or charge on the inhaler capacitor for the recharge). However, preferably, the refill pack has a pressure or electrical mechanism to disengage the inhaler from the position in which it is refilled and recharged after a predetermined period of time.

The heater is preferably configured to heat the composition to a temperature that will volatilise some, but not all, of the components of the composition. This means that the temperatures required are less than those of the prior art. This further reduces the power requirement of the E-cigarette and prevents the degradation of the inhaled formulation. Thus, preferably, the heater is arranged to heat the composition to between 40 and 180° C. and preferably 40° C. to 100° C. The ability to dispense at these temperatures is based on a recognition by the inventors that it is not necessary to volatilise all components of the formulation. Instead, the temperature is set at a level at which only certain components of the composition (such as ethanol) will volatilise.

Additionally or alternatively, other mechanisms may be employed to effect a fine aerosolisation of the non-volatilised formulation components. For example, the composition may include a propellant to increase the pressure in the reservoir resulting in improved aerosolisation.

Additionally or alternatively there may be at least one airflow path arranged to draw air in through the side of the cigarette as a user inhales from an inhaling end, and impinge on the composition leaving the heater at the inhaling end. Such airflow will reduce the mean particle size of the plume. Preferably there is more than one such path, and preferably the paths are arranged to generate swirl around the main axis of the inhaler thereby generating further turbulence and causing greater reduction in particle size.

The airflow paths are preferably arranged to pass through a constriction in the vicinity of the outlet end of the inhaler thereby generating a Venturi effect and promoting suction of the composition out of the inhaler. The inhaler may be configured to have a throughflow of air from one end to the other when the user inhales from the outlet end. However, preferably, one or both of the effect of the propellant in the reservoir and the Venturi effect provided by the airflow paths provides the motive force to expel the composition from the reservoir.

The present invention also extends to an inhaler for use with the above refill pack, the inhaler comprising a reservoir for an inhalable composition, a heating element and/or vibrating transducer to volatilise at least some components of the composition, and at least one inhaler capacitor arranged to supply electrical power to the heater and/or vibrating transducer when the user inhales from the cigarette, the reservoir being refillable and the inhaler capacitor being rechargeable from a battery external to the inhaler, without disassembling the inhaler.

The inhaler preferably has all of the above-mentioned preferred features attributable to the inhaler. In particular, it preferably has a pressured reservoir. This is preferably pressurised by a propellant which is preferably HFA.

The invention also extends to a refill pack for refilling and recharging an inhaler, the refill pack comprising a refill reservoir of an inhalable composition and a battery coupled to a refill capacitor, and a pack being arranged to engage with an inhaler to simultaneously refill the inhaler with inhalable composition and recharge the inhaler.

The refill pack preferably has the preferred features mentioned above attributable to the refill.

The present invention also extends to a method of refilling and recharging an inhaler comprising a reservoir for an inhalable composition, a heating element and/or vibrating transducer to selectively volatilise at least some components of the composition and at least one inhaler capacitor arranged to selectively supply electrical power to the heater when a user inhales from the inhaler, the method comprising engaging the inhaler with a refill pack comprising a reservoir of inhalable composition and a battery and/or vibrating transducer coupled to a refill capacitor, causing the refill reservoir to refill the inhaler reservoir and the inhaler capacitor to be simultaneously recharged from the refill capacitor.

An example of a combination of an inhaler and refill pack will now be described with reference to the accompanying drawings, in which.

The inhaler described below is one which uses a heating element in order to (at least partially) volatilise the composition. There may, alternatively or additionally, be a vibrating transducer such as a Plezo-electric or ultrasonic transducer which is provided in place of or in addition to the heater to volatilise the composition.

The inhaler is in the form of a simulated cigarette having a generally cylindrical configuration the approximate size of a cigarette.

The inhaler has a cylindrical housing 1 which may be in one or more parts. The housing may be wrapped with a paper-like wrap to provide a more realistic cigarette-like appearance and feel.

Figure 1:
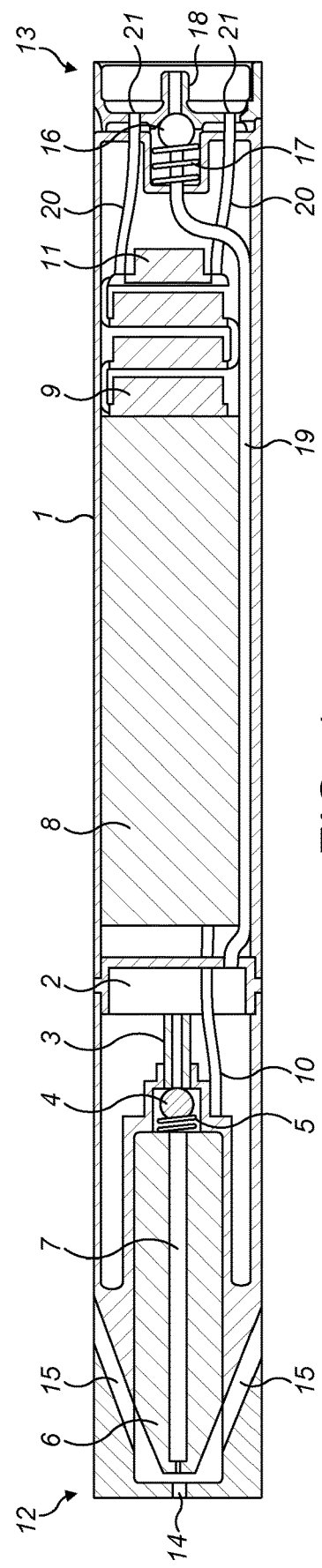
FIG. 1 is a schematic cross-section of an inhaler.

Within the housing 1 is a reservoir 2 of inhalable composition. The reservoir 2 has an outlet 3, flow from which is controlled by a ball valve 4 which is opened by an electromagnetic actuator against the action of a spring 5 which biases the ball valve 4 onto the outlet 3. As an alternative the outlet valve may be a breath operated valve as disclosed in WO 2011/015825 and WO 2014/033438. Downstream of the ball valve 4 is a heater 6. This is made of any highly efficient conductive material, preferably fibreglass, and has an internal pathway 7 along its central axis for the passage of composition. The heating element 6 is powered by a super capacitor 8 (also known as an ultra-capacitor). A suitable capacitor is sold by Maxwell Technologies as part of the HC series. This preferably has a capacity of 3-7 F and a diameter of 6 mm to 10 mm and a length of 5 to 50 mm. There may be more than one capacitor provided. FIG. 1 also shows an optional battery 9 which will charge the capacitor 8. However, the current preference is for no battery to be present. The capacitor 8 is connected to the heater 6 by a wire 10. Circuitry 11 is provided to control the operation of the inhaler.

The inhaler has an inhaling end 12 and a refill end 13. The inhaling end is provided with an outlet orifice 14 which is in communication with the internal pathway 7 from the heater. Surrounding the heater 6 in the vicinity of the inhaling end 12 are a number of air paths 15 as shown in FIG. 1. In practice, there may be a number of air paths arranged around the axis, but there are preferably 2 to 4 such passages. These are angled with respect to the main axis of the inhaler as shown. They are also be offset with respect to the axis such they general swirl of the air about the main axis. In particular, the air paths 15 are configured to generate a Venturi effect causing suction in the internal pathway 7 of the heater 6 when a user inhales from the inhaling end 12.

The refill end is provided with a refill valve 16 in the form of a ball valve which opens against the action of a spring 17 which biases the valve closed onto a refill nozzle 18. The refill valve 16 is connected to the reservoir 2 by a refill conduit 19 which extends past the capacitor 8 to provide fluid communication between the refill nozzle 18 and the reservoir 2. A pair of electrical contacts 20 with exposed ends 21 are arranged to provide an electrical connection from the refill end 13 to the opposite terminals of the capacitor 8.

When a user inhales from the inhaling end 12, air flow is detected by a sensor switch (not shown) in the airflow path 15 triggering the current flow from the capacitor 8 to the heater 6 in order to heat the composition. The composition comprises ethanol (boiling point 78.4° C.), nicotine (boiling point 247° C.), propylene glycol (boiling point 188° C.) and HFA (boiling point −26° C.). Thus, by heating the composition to a temperature of under 180° C., all but the nicotine and propylene glycol are volatilised. Preferably the composition is heated to 80° C. which will comprise the ethanol but not the propylene glycol. The result of this heating is a mixture of non-volatilised liquid formation and vapour.

At the same time, the ball valve 4 is opened by the electromagnetic actuator. Thus, the composition in the reservoir 2, which may be pressurised to for example, 6 bar if a propellant is used, leaves the reservoir along the internal pathway 7 assisted by the suction force generated by the airflow in the air paths 15. This airflow also serves to break up the composition ensuring that the plume emitted from the outlet orifice 4 has a fine aerosolisation that promotes higher pulmonary deposition.

The refill pack will now be described by reference to FIG. 2. This shows the inhaler of FIG. 1 inserted into the refill pack with the refill end 13 lowermost. The refill pack is approximately the size and shape of a standard cigarette pack but can have any configuration.

The refill pack comprises a housing 30 and is broadly divided into three sections namely, from left to right (in FIG. 2), a storage port 31 to receive the inhaler, a power supply 32 and a composition refill 33. These are connected across the base of the housing 30 as described below.

Figure 3:
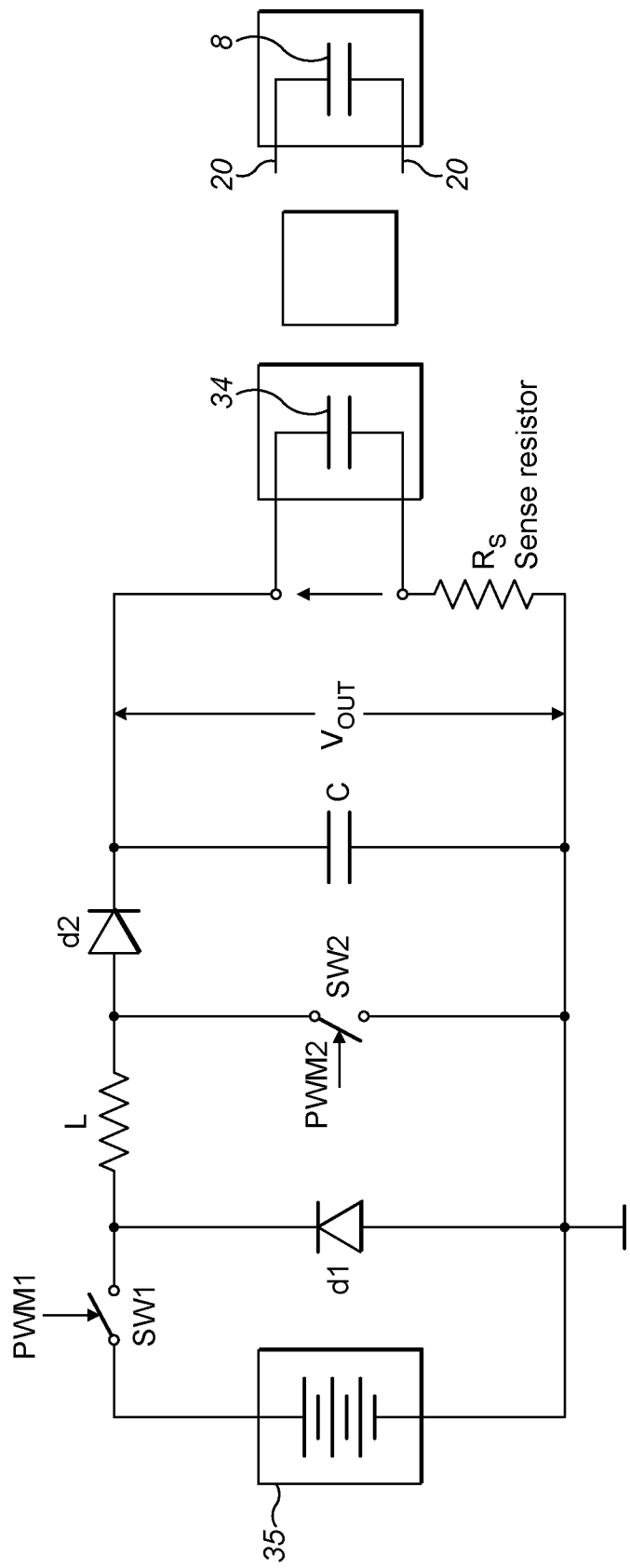
FIG. 3 is a circuit diagram for the recharging operation.

The power supply 32 comprises a capacitor 34 which is charged from the battery 35 as shown in FIG. 3. Control circuitry 36 is retained in place by a screw cap 37. The reservoir 33 is pressurised by a plunger 38 which is biased downwardly by a spring 39 held in place by a screw cap 40. The bottom end of the reservoir is connected by a refill duct 41 to a refill valve 42 beneath the inhaler port 31. The refill valve 42 is a ball valve which is biased closed by a spring and which is opened, in use, by the refill nozzle 18 of the inhaler which presses downwardly on the refill valve 42.

A release spring 43 is provided in the housing 30 underneath the inhaler recess 31. This spring will push the inhaler away from the refilling position to a storage position when the refilling process is complete. This may be done, for example, by releasing the inhaler when a certain priority is detected which indicates that the refill operation is complete.

Figure 2:
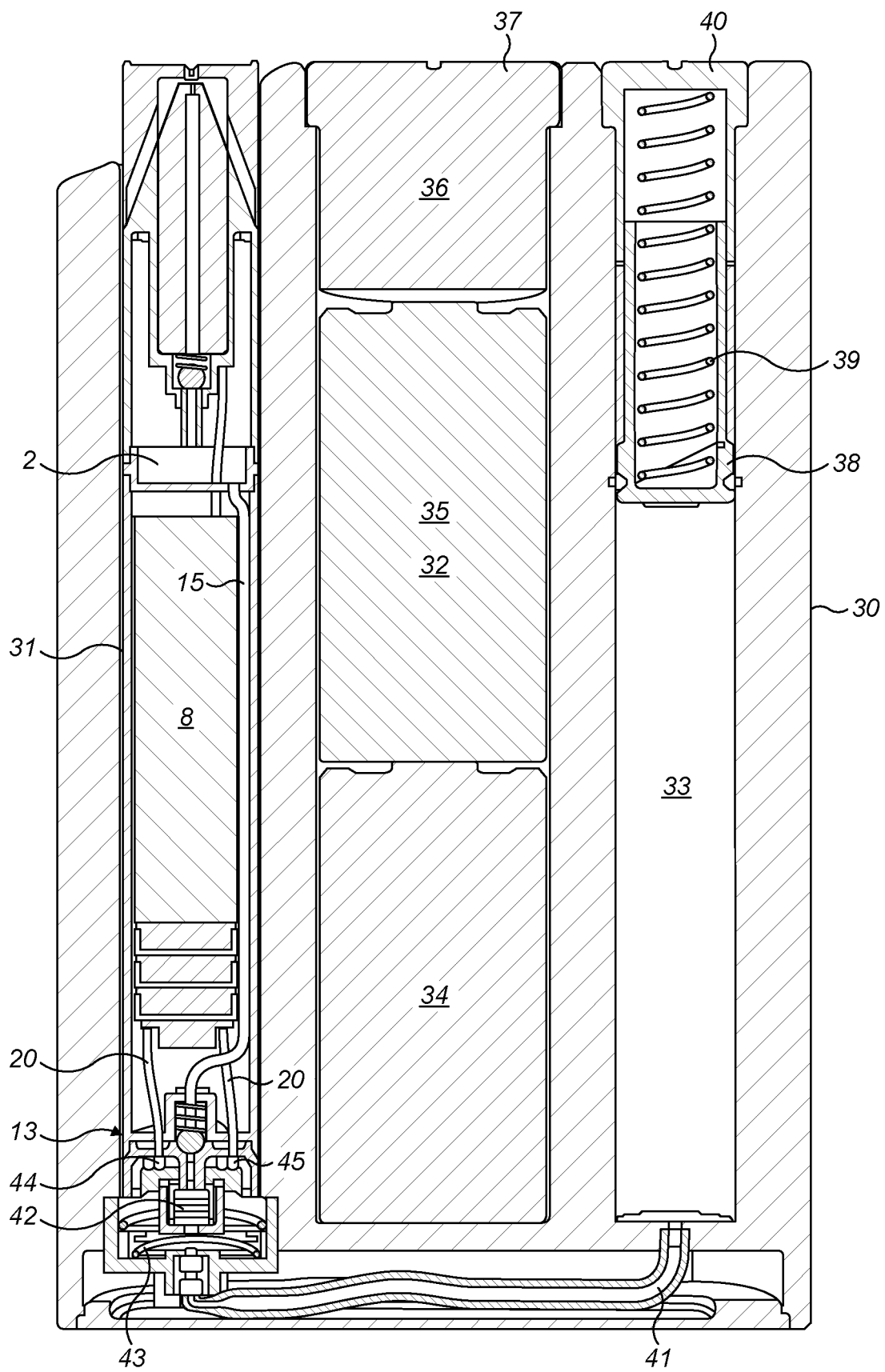
FIG. 2 is a schematic cross-section of an inhaler within a refill pack.

When the reservoir 2 is depleted of composition, the inhaler is inserted into the housing 30 in the orientation as shown in FIG. 2 and downward pressure is applied to overcome the release spring 42. The refill nozzle 18 opens the refill valve 42 such that the pressure in the reservoir 33 is sufficient to lift the refill valve 16 in the inhaler thereby allowing composition to flow along the refill conduit 19 and link to the reservoir 2. The refill operation is automatically terminated as described above and the release spring urges the inhaler to the storage position.

At the same time as the inhaler is being refilled, the ends 21 of the electrical contacts 20 make contact with inner 44 and outer 45 charging plate rings in the housing 30 which are electrically coupled to the capacitor 43. This causes the inhaler capacitor 8 to be recharged simultaneously with the refill. The recharge circuit is shown in FIG. 3.

The invention claimed is:

1. A combination of an inhaler and a refill pack, the inhaler comprising a pressurized reservoir pressurised with a propellant or a compressed gas and an inhalable composition, a heating element and/or vibrating transducer to selectively volatilise at least some components of the composition and at least one inhaler capacitor arranged to supply electrical power to the heater and/or vibrating transducer when a user inhales from the inhaler; the refill pack comprising a pressurized refill reservoir of inhalable composition and a battery coupled to a refill capacitor, wherein the refill pack is arranged to engage with the inhaler to simultaneously refill the reservoir and fully recharge the inhaler capacitor in less than 30 seconds.

2. A combination according to claim 1, wherein the pack is arranged to fully recharge and refill the inhaler from empty in less than 10 seconds.

3. A combination according to claim 1, wherein the inhaler capacitor is the sole electrical power source on the device.

4. A combination according to claim 1, wherein the total capacitance of the inhaler is IF to 350 F, preferably 1 to 50 F and more preferably 3 F to 7 F.

5. A combination according to claim 1, wherein at least one of the inhaler and refill capacitors is a super capacitor.

6. A combination according to claim 1, wherein the battery is non-rechargeable.

7. A combination according to claim 1, wherein the device reservoir having a closable refill valve and the refill pack having a complementary refill valve such that engagement of the device with the pack will cause the two refill valves to open thereby allowing the pressurized composition to flow into the inhaler reservoir.

8. A combination according to claim 1, wherein the refill pack is configured such that it will automatically terminate the refill and recharge operations.

9. A combination according to claim 8, wherein the refill pack has a mechanism to disengage the inhaler from the position in which it is refilled and recharged after a predetermined period of time.

10. A combination according to claim 1, wherein the heater is configured to heat the composition to a temperature that will volatilise some, but not all of the components of the composition.

11. A combination according to claim 10, wherein the heater is arranged to heat the composition to between 40 and 180° C. and preferably between 40 and 100° C.

12. A combination according to claim 1, wherein the heater is arranged to heat the composition after it has left the reservoir.

13. A combination according claim 1, wherein the inhaler further comprises at least one airflow path arranged to draw air in through the inhaler as a user inhales from an inhaling end, and impinge on the composition leaving the heater at the inhaling end.

14. A combination according to claim 13, wherein there is more than one path and wherein the paths are arranged to generate a swirl around the main axis of the inhaler.

15. A combination according to claim 13, wherein there is more than one path and wherein the airflow paths are arranged to pass through a constriction in the vicinity of the outlet end of the inhaler thereby generating a Venturi effect and promoting suction of the composition out of the inhaler.

16. A refillable and rechargeable inhaler comprising a reservoir pressurised with a propellant or a compressed gas and an inhalable composition, a heating element and/or vibrating transducer to volatilise at least some components of the composition, and at least one inhaler capacitor arranged to supply electrical power to the heater and/or vibrating transducer when the user inhales from the inhaler, the reservoir being refillable and pressurized and the inhaler capacitor being rechargeable from a refill capacitor external to the inhaler, without disassembling the inhaler.

17. An inhaler according to claim 16, wherein the inhaler is a simulated cigarette.

18. An inhaler according to claim 16, wherein the propellant is HFA.

19. A refill pack for refilling and recharging an inhaler, the refill pack comprising a pressurized refill reservoir pressurised with a propellant or a compressed gas and an inhalable composition and a battery coupled to a refill capacitor, and the pack being arranged to engage with an inhaler to simultaneously refill the inhaler with inhalable composition and recharge an inhaler capacitor from the refill capacitor wherein both the refilling and recharging are completed in under 30 seconds.

20. A method of refilling and recharging an inhaler comprising a pressurized reservoir pressurised with a propellant or a compressed gas and an inhalable composition, a heating element and/or vibrating transducer to selectively volatilise at least some components of the composition and at least one inhaler capacitor arranged to supply electrical power to the heater and/or vibrating transducer when a user inhales from the inhaler, the method comprising engaging the inhaler with a refill pack comprising a pressurized reservoir of inhalable composition and a battery coupled to a refill capacitor, causing the refill reservoir to refill the inhaler reservoir and the inhaler capacitor to be simultaneously recharged from the refill capacitor wherein refilling and recharging are completed within 30 seconds.

* * * * *